United States Patent [19]

Sampathkumar

[11] Patent Number: 5,028,414

[45] Date of Patent: Jul. 2, 1991

[54] ANAEROBE-SELECTIVE ANTIBACTERIAL COMPOSITIONS AND METHODS

[75] Inventor: Padmini Sampathkumar, Fairfield, Ohio

[73] Assignee: The Procter & Gamble Company, Cincinnati, Ohio

[21] Appl. No.: 272,669

[22] Filed: Nov. 17, 1988

Related U.S. Application Data

[62] Division of Ser. No. 75,235, Jul. 17, 1987, Pat. No. 4,804,530.

[51] Int. Cl.$^5$ .................. A61K 7/16; A61K 7/18; A61K 9/68
[52] U.S. Cl. ..................... 424/53; 424/43; 424/44; 424/48; 424/49; 424/52; 424/55; 424/464; 514/900; 514/901; 514/902; 514/557; 514/558
[58] Field of Search ............. 424/48, 49, 52, 53, 424/55, 58, 464, 43, 44; 514/900–902, 557–558

[56] References Cited

U.S. PATENT DOCUMENTS

| | | | |
|---|---|---|---|
| 3,988,433 | 10/1976 | Benedict | 424/53 |
| 4,100,095 | 7/1978 | Hutchins et al. | 252/99 |
| 4,154,695 | 5/1979 | McCrudden et al. | 252/99 |
| 4,259,201 | 3/1981 | Cockrell et al. | 252/99 |
| 4,350,681 | 9/1982 | Fulton | 424/53 |
| 4,363,322 | 12/1982 | Andersson | 128/290 R |
| 4,370,251 | 1/1983 | Liao et al. | 252/186.42 |
| 4,483,781 | 11/1984 | Hartman | 252/174.12 |
| 4,627,977 | 12/1986 | Gaffar | 424/52 |
| 4,670,252 | 6/1987 | Sampathkumar | 424/53 |
| 4,804,530 | 2/1989 | Sampathkumar | 514/901 |

FOREIGN PATENT DOCUMENTS

| | | |
|---|---|---|
| 1141702 | 1/1969 | United Kingdom . |
| 1477691 | 6/1977 | United Kingdom . |
| 1565672 | 4/1980 | United Kingdom . |
| 2110088 | 6/1983 | United Kingdom . |

OTHER PUBLICATIONS

*Hack's Chemical Dictionary*, 4th ed., ed. by Grant, McGraw-Hill Book Co., N.Y., 1969, p. 617.

*Primary Examiner*—Ronald W. Griffin
*Attorney, Agent, or Firm*—Milton B. Graff, IV; Kim William Zerby; George W. Allen

[57] ABSTRACT

This invention relates to pharmaceutical compositions comprising anaerobe-selective antibacterial agents which are substituted or unsubstituted, 1,12-dodecanedioic peroxy acids, or their pharmaceutically-acceptable salts or esters. The pharmaceutical compositions of the present invention are especially suitable for oral administration in the form of mouth rinses and toothpastes. These anaerobe-selective antibacterial compositions are useful for treating or preventing anaerobic bacterial infections, especially diseases of the oral cavity, in humans or lower animals.

The present invention further relates to a method for treating or preventing anaerobic bacterial infections such as acne, and especially diseases of the oral cavity such as gingivitis and periodontal disease, in humans or lower animals. The method comprises topically contacting the anaerobe-containing tissue of the human or lower animal with a safe and effective amount of an anaerobe-selective antibacterial agent selected from substituted or unsubstituted 1,12-dodecanedioic peroxy acids, or their pharmaceutically-acceptable salts or esters.

8 Claims, No Drawings

ANAEROBE-SELECTIVE ANTIBACTERIAL COMPOSITIONS AND METHODS

This is a division of application Ser. No. 075,235, filed on July 17, 1987, now U.S. Pat. No. 4,804,530.

BACKGROUND OF THE INVENTION

This invention relates to pharmaceutical compositions, especially pharmaceutical compositions suitable for oral administration such as mouth washes and toothpastes, which are useful for treating or preventing anaerobic bacterial infections, especially diseases of the oral cavity, in humans or lower animals. This invention further relates to a method for treating or preventing anaerobic bacterial infections, especially diseases of the oral cavity such as gingivitis and periodontal disease, as well as acne, in humans or lower animals.

Virtually all anaerobic infections arise endogenously. Anerobic bacteria are a part of the normal flora of the skin. They also exist prevalently on all mucosal membrane surfaces as endogenous flora. Given the proper circumstances and opportunity to penetrate tissues, anaerobes from the endogenous flora set up infections, such as gas gangrene, vulvovaginal abscess, chronic sinusitis, and Vincent's disease.

Periodontal diseases are believed to involve anaerobic bacterial infection. Periodontal disease affects the periodontum, which is the investing and supporting tissues surrounding a tooth (i.e., the periodontal ligiment, the gingiva, and the alveolar bone). Gingivitis and periodontitis are inflammatory disorders of the gingiva and the periodontal ligiment, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at about age 35, but even by about age 15, it is estimated that about 4 out of 5 persons already have gingivitis and about 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms, especially anaerobes, contribute to both the initiation and progress of periodontal disease. Thus, in order to prevent or treat periodontal disease, these microorganisms must be suppressed by some means other than simple mechanical scrubbing.

It is known that certain anaerobe infections may be treated with some degree of effectiveness with hyperbaric oxygen or hydrogen peroxide. Other forms of treatment with oxygen or oxygen compounds are also known in the art. For example, U.S. Pat. No. 3,988,433, to Benedict, issued Oct. 26, 1976, discloses short-chain alkyl diperoxy acids, and meta- or parasubstituted aromatic peroxy acids as being useful for preventing or removing stains from teeth. These organic peroxy acids are also disclosed as being antibacterial agents for controlling the bacterial population in the mouth.

British Patent No.1,565,672, to Goupil, published Apr. 23, 1980, discloses a toothpaste which generates oxygen. It is useful for prophylaxis and treatment of bucco-dental infections.

U.S. Pat. No. 4,350,681, to Fulton, issued Sept. 21, 1982, discloses benzoyl peroxide which is stabilized by glycerol dispersed in an aqueous medium. A combination of this mixture with a mild abrasive, wetting agent, and thickener, adjusted to pH between 3.5 and 5.0 is suitable for use as a toothpaste. It is disclosed to be an antibacterial for gingival inflammation.

In spite of the large amount of research aimed at developing antibacterial compositions such as acne cleansers, therapeutic dentifrices, and mouth washes, there is a continuing need to identify additional safe and effective antibacterial compositions.

It is therefore an object of the present invention to provide pharmaceutical compositions which are useful for treating or preventing anaerobic bacterial infection in humans or lower animals. In particular, it is a further object of this invention to provide oral pharmaceutical compositions, such as mouth washes and toothpastes, which are useful for treating or preventing diseases of the oral cavity, such as gingivitis and periodontitis, in humans or lower animals; and further which are cosmetically acceptable.

It is a further object of the present invention to provide a method for treating or preventing anaerobic bacterial infections, especially diseases of the oral cavity, in humans or lower animals.

SUMMARY OF THE INVENTION

The present invention provides pharmaceutical compositions which are highly efficacious and selective in killing anaerobic bacteria. Such compositions of the present invention comprise from about 0.001% to about 99.9% by weight of an anaerobe-selective antibacterial agent and from about 0.1% to about 99.999% of a pharmaceutically-acceptable carrier. The anaerobe-selective antibacterial agent is selected from substituted or unsubstituted 1,12-dodecanedioic peroxy acids, or their pharmaceutically-acceptable salts and esters. These anaerobe-selective antibacterial compositions can be prepared in the form of acne cleansers, and especially oral pharmaceutical compositions, such as toothpastes and mouthrinses.

The present invention further relates to a method for treating or preventing anaerobic bacterial infections such as acne, and especially diseases of the oral cavity, such as gingivitis and periodontal disease, in humans or lower animals. This method comprises topically contacting the anaerobe-containing tissue of the human or lower animal (e.g. the oral cavity or skin) with a safe and effective amount of an anaerobe-selective antibacterial agent which is a substituted or unsubstituted 1,12-dodecanedioic peroxy acid, or its pharmaceutically-acceptable salts or esters.

DETAILED DESCRIPTION OF THE INVENTION

The present invention is based on the surprising discovery that the 1,12-dodecanedioic peroxy acids, and their pharmaceutically acceptable salts and esters, are very effective antibacterial agents which are furthermore highly selective in their activity against anaerobic bacteria, and especially the anaerobic bacteria found in the mouth. The unexpected nature of this discovery is shown by the significantly greater antibacterial activity and selectivity of the compounds useful in the present invention (e.g., diperoxy 1,12-dodecanedioic acid) in comparison with the antibacterial activity and selectivity of compounds which have very similar chemical structures (e.g., the known antibacterial agents diperoxyadipic acid, diperazelaic acid, and dipersebacic acid). Such comparative antibacterial activity is shown in Table 1 wherein antibacterial activity of various peroxy acids against both anaerobes (F. nucleatum) and aerobes (S. mutans) is demonstrated.

TABLE 1

Antibacterial Activity and Selectivity of Aliphatic Mono- and Diperoxy Acids

| Peroxy Acid | Antibacterial Activity[a] (log colony reduction/ min/ppm AvO) | | Anaerobe Selectivity F. nucleatum/ |
| --- | --- | --- | --- |
| | F. nucleatum | S. mutans | S. mutans) |
| $HO_3C(CH_2)_{10}CO_3H$* | 500 | 18 | 25:1 |
| $HO_3C(CH_2)_9CO_3H$ | 40 | 60 | 1:1.5 |
| $HO_3C(CH_2)_7CO_3H$ | 10 | 60 | 1:6 |
| $HO_3C(CH_2)_6CO_3H$ | 5 | 20 | 1:4 |
| $HO_3C(CH_2)_4CO_3H$ | 5 | 20 | 1:4 |
| $CH_3(CH_2)_{10}CO_3H$ | 100 | 150 | 1:1.5 |
| $CH_3(CH_2)_8CO_3H$ | 50 | 80 | 5:8 |
| $CH_3(CH_2)_6CO_3H$ | 20 | 40 | 1:2 |

*diperoxy, 1,12-dodecanedioic acid
[a]log colony reduction/min/ppm AvO = calculated by extrapolation from the initial slope (log colony reduction/min) of the plot of log colony reduction (e.g., a 7 log colony reduction is $10^7$ reduction in number of live bacteria) versus time of exposure to the peroxy acid, this slope then being divided by the concentration (in ppm of available oxygen) of the peroxy acid used; the experiments used 7 logs of F. nucleatum and 5 logs of S. mutans as the number of bacteria present before active was added, with the reduction in live bacteria after active was added being measured over about a 15 minute period.

It is clear from the activity and selectivity data provided in Table 1 that diperoxy 1,12-dodecanedioic acid has far greater activity, and far greater selectivity, against anaerobes vs. aerobes, than any of the shorter chain alkyl peroxy acids, including peroxy acids known to be useful as antibacterial agents. Furthermore, it can be seen from the Table 1 data that low concentrations of diperoxy 1,12-dodecanedioic acid are very efficacious and highly selective in combatting the types of anaerobic bacteria which are implicated in gingivitis, periodontitis, and other serious anaerobe infections.

The 1,12-dodecanedioic peroxy acids of the present invention are particularly well suited for treating or preventing diseases of the oral cavity. This is so for several reasons. In the first place, 1,12-dodecanedioic peroxy acids, and in particular unsubstituted diperoxy 1,12-dodecanedioic acid, are relatively stable to enzymatic decomposition in the oral cavity, unlike, for example, hydrogen peroxide. In addition, the antibacterial agents of the present invention are effective in vivo at penetrating through the layer of mucus, tissue and aerobic bacteria in the mouth to reach and kill the anaerobic bacteria underneath. Furthermore, the antibacterial agents of the present invention not only selectively combat the anaerobic bacteria, such agents also suppress regrowth of these bacteria. Finally, at concentrations above about 0.1% by weight in aqueous ethanol solution (15% ethanol in water), the particular antibacterial agents of this invention are believed to provide anticaries benefits.

The above noted selectivity of 1,12-dodecanedioic peroxy acids for combatting anaerobes is desirable in the treatment of anaerobe infections. This selectivity avoids destroying all the normal flora of the infected tissue. By contrast, broad spectrum anti-bacterials, which destroy all of the normal flora, create the potential for diseases that such normal flora may act to prevent, such as yeast infections. Thus, the anaerobe selectivity of the antibacterial agents used in the present invention allows part of the normal flora to survive while destroying pathogenic anaerobes.

In treating diseases of the oral cavity, selectivity against anaerobes is particularly desirable for cosmetic reasons. Broad spectrum antibacterials, such as chlorhexidine, can cause tooth staining which is believed to be a direct result of destroying substantially all of the bacteria in the mouth. The anaerobe selectivity of the particular peroxy acids used in the present invention should be effective for treating diseases of the oral cavity without causing the undesirable staining of the teeth. In addition, since such peroxy acids are also bleaching agents, there may also be stain removal benefits when such peroxy acids are applied to teeth.

Pharmaceutical Compositions a. Anaerobe-Selective Antibacterial Agent

The anaerobe-selective antibacterial agent utilized as the active component in the pharmaceutical compositions of the present invention comprises a substituted or unsubstituted 1,12-dodecanedioic peroxy acid. Pharmaceutically-acceptable salts or esters of such acids may also be employed. The term "pharmaceutically-acceptable salts or esters" as used herein means salts or esters of the substituted or unsubstituted 1,12-dodecanedioic peroxy acid which have the same general antibacterial properties as diperoxy 1,12-dodecanedioic acid, and which are acceptable from a toxicity viewpoint. Non-limiting examples of pharmaceutically-acceptable salts include alkali metal (i.e., sodium, potassium), alkaline earth metal (i.e., calcium, magnesium), non-toxic heavy metal, ammonium, and trialkyl ammonium (i.e., trimethyl ammonium). Non-limiting examples of pharmaceutically-acceptable esters are the methyl and ethyl mono- and di-esters.

The straight chain 1,12-dodecanedioic peroxy acid antibacterial agent may be substituted with one or more substituents selected from the group consisting of straight or branched chain alkyl groups having from 1 to 6 carbon atoms (preferably methyl or ethyl), phenyl, benzyl, chloro, fluoro, nitro, trifluoromethyl, trimethyl ammonium, carboxy, percarboxy, or mixtures thereof. Generally, no more than about 2 of the carbon atoms in the 1,12-dodecanedioic acid chain will be substituted.

Preferably, the 1,12-dodecanedioic acid chain is unsubstituted (i.e., $-(CH_2)_{10}-$). In addition, it is preferred that the anaerobe-selective antibacterial agent be the diperoxy acid (i.e., $HO_3C(CH_2)_{10}CO_3H$). However, it is to be understood that a peroxy acid of unsubstituted or substituted 1,12-dodecanedioic acid may also be a compound having only one peroxy acid group per molecule at either the 1 or 12 position, provided there is a carboxylic acid or carboxylate group at the other end of the carbon chain, e.g., $HO_2C(CH_2)_{10}CO_3H$. The pharmaceutical compositions herein may also comprise mixtures of diperoxy and monoperoxy 1,12-dodecanedioic acid, and/or the pharmaceutically-acceptable salts or esters of such acids.

The peroxy acid antibacterial agents of the present invention are known compounds. They may be synthesized by known methods such as methods disclosed in, e.g., U.S. Pat. No. 4,483,781, to Hartman, issued Nov. 20, 1984; and in U.S. Pat. No. 3,988,433, to Benedict, issued Oct. 26, 1976. The disclosures of both these patents are incorporated herein by reference.

The anaerobe-selective antibacterial agent will generally comprise from about 0.001% to about 99.9% by weight of the pharmaceutical compositions of the present invention, more preferably from about 0.1% to about 80% by weight of the compositions. Depending on the form of the pharmaceutical composition (e.g., tablet; paste; solution) and the intended use of the composition (e.g., toothpaste; mouth rinse; body scrub), preferred concentrations of the anaerobe-selective antibacterial agent will fall within ranges more narrowly set for these individual types of compositions. Preferred active concentration ranges for such particular types of compositions are discussed in greater detail hereinafter.

b. Pharmaceutically-Acceptable Carrier

In addition to the anaerobe-selective antibacterial agent, the pharmaceutical compositions herein essentially contain a pharmaceutically-acceptable carrier. The term "pharmaceutically-acceptable carrier", as used herein, means one or more compatible solid or liquid filler diluents or encapsulating substances which are suitable for delivering the anaerobe-selective antibacterial agent to the site in or on the human or animal body wherein an anaerobic bacterial infection is to be combatted. The term "compatible", as used herein, means that the components of the carrier must be capable of being comingled with the active and with each other in a manner such that there is no interaction which would substantially reduce during use the composition's efficacy for treating or preventing anaerobe infections. Pharmaceutically-acceptable carriers, of course, must be of sufficiently high purity and sufficiently low toxicity to render them suitable for administration to the human or lower animal body.

The pharmaceutical compositions of the present invention contain pharmaceutically-acceptable carriers selected as appropriate for the method of composition administration and for the part of the body to be treated with the composition. Thus, if the composition is to be used as, e.g., a vaginal douche, a body rinse for acne, or a mouth rinse for gingivitis, it is preferred that the composition be formulated with solid components that dissolve rapidly in the water (or, typically for mouth rinses, in ethanol-water) media used to form a solution for administering the composition. Creams or gels would be useful, e.g., for treating acne; and toothpastes, tooth powders, tooth gels, mouth sprays, lozenges, chewing gums, and sachets, would be useful in the oral cavity.

The pharmaceutically-acceptable carriers for the pharmaceutical compositions of the present invention to be used in the oral cavity can include the usual and conventional components of toothpastes, toothpowders, toothpaste gels, mouth rinses, mouth sprays, chewing gums, lozenges, and sachets as are more fully described hereinafter. Generally, however, the pharmaceutically-acceptable carriers should be materials which are free of reactive hydroxyl groups and normally also to materials which do not contain other reactive sites, such as for example, amino, amido, iodo, bromo, and sulfhydryl groups, and unsaturated, imino, and thioether linkages if the composition is to be stored for any appreciable period of time. Thus, it is preferred that the compositions of the present invention be totally or substantially anhydrous until just prior to use. Water can then be added to the composition just prior to use, for example, by dissolving the anhydrous pharmaceutical composition in water.

It is contemplated, however, that even reactive carriers may be used in formulating the compositions of the present invention when the reactive carrier is partitioned or stored separately from the peroxy acid antibacterial agent, and the product is used immediately after the components are combined. For example, toothpaste compositions conventionally contain abrasive materials, sudsing agents, binders, humectants, flavoring and sweetening agents. Most of these cannot be maintained in contact with the peroxy acid antibacterial agents for substantial periods of time. Therefore, components of toothpaste compositions of the present invention will normally be partitioned in separate containers or chambers, to be combined just before use. Compatible additives and actives (e.g., water-soluble fluoride) may be combined with the peroxy acid active-containing component of the compositions herein.

Dentifrice compositions (e.g., toothpastes; toothgels; and toothpowders) generally comprise, in addition to the anaerobe-selective peroxy acid antibacterial agent, a pharmaceutically-acceptable carrier which can comprise the usual and conventional components of dentifrice compositions. U.S. Pat. No. 3,988,433, to Benedict, issued Oct. 26, 1976 provides specific disclosure of such usual and conventional pharmaceutically-acceptable carriers. The disclosure of this patent is incorporated herein by reference. Generally the dentifrices of the present invention may include abrasive polishing material, flavoring agents, sweetening agents, coloring agents, emulsifying agents, water-soluble fluorides, thickening agents, humectants, alcohols, and/or water, with any carriers unsuitable for storage stability when combined with the peroxy acid antibacterial agent being stored separately as noted hereinbefore.

Typically, the dentifrice compositions of the present invention comprise anaerobe-selective antibacterial agent in an amount of from about 0.01% to about 50%, preferably from about 0.01% to about 35%, more preferably from about 1% to about 35%, by weight of the composition. Accordingly, the pharmaceutically-acceptable carrier components of the dentifrice compositions will generally comprise from about 50% to about 99.99%, preferably from about 65% to about 99.99%, more preferably from about 65% to about 99%, by weight of the composition.

Typically, such dentifrice compositions comprise, as part of the pharmaceutically-acceptable carrier, water-soluble fluoride in an amount of from about 0.0025% to about 5%, preferably from about 0.005% to about 2%, by weight of the dentifrice composition to provide additional anticaries effectiveness. Preferred water-soluble fluoride compounds are sodium fluoride, stannous fluoride, indan fluoride, and sodium monofluorophosphate. Further preferred as part of the pharmaceutically-acceptable carrier for the dentifrices of the present invention is dental abrasive polishing material comprising, by weight, from about 0.5% to about 95%, preferably from about 10% to about 60%, of the dentifrice compositions.

Mouth rinse compositions of the present invention are frequently in the form of anhydrous solid powder, tablet, or capsule concentrates which dissolve rapidly in water. Mouth rinse compositions may also be in the form of an ethanol-water mixture (ethanol: water ratio from about 1:20 to about 1:2 on a volume to volume basis; preferred being 15% ethanol solution). It is also preferred that the concentrate be formulated to include as part of the pharmaceutically-acceptable carrier an effervescing agent and/or surfactant (preferably a nonionic surfactant) to facilitate rapid disintegration of the solid and dissolution into the aqueous carrier, as well as a chelating agent. Preferred effervescing agents are mixtures of carbonate and citrate or bicarbonate and citrate. The present invention includes both the mouth rinse concentrate and the aqueous ethanol mouth rinse solution.

Mouth rinse compositions generally comprise in addition to the anaerobe-selective antibacterial agent a pharmaceutically acceptable carrier which can comprise other ingredients which are typically found in mouth rinses, e.g., flavor and sweetening agents, humectants, sudsing agents, coloring agents, abrasives, etc., as well as the above noted effervescing agents. As noted above, it may be necessary to keep some or all of the pharmaceutically-acceptable carrier components separated from the peroxy acid antibacterial agent until just prior to use in order to preserve the storage stability of the composition. U.S. Pat. No. 3,988,433, to Benedict, issued Oct. 26, 1976, provides disclosure concerning the preparation of mouth rinse compositions of the type contemplated by the present invention. The disclosure of this patent is incorporated herein by reference.

Typically, anhydrous mouth rinse concentrate compositions of the present invention comprise anaerobe-selective antibacterial agent and pharmaceutical carrier in the same concentrations as in the dentifrice compositions described hereinbefore. On the other hand, aqueous mouth rinse solutions of the present invention comprise anaerobe-selective antibacterial agent in an amount of from about 0.001% to about 10%, more preferably from about 0.01% to about 1%, and most preferably from about 0.05% to about 0.5%, by weight of the composition. The aqueous carrier in such compositions will generally comprise ethanol/water mixtures, and will be present in an amount of from about 90% to about 99.999%, more preferably from about 99% to about 99.99%, and most preferably from about 99.5% to about 99.95%, by weight of the composition.

Preparation of compositions of the present invention in the form of mouth sprays, lozenges, chewing gums, sachets, creams, gels, powders, body rinses, body lotions, etc. can readily be achieved by one of ordinary skill in the art using the teachings disclosed hereinbefore and the teachings in, for example, U.S. Pat. No. 3,988,433, to Benedict; U.S. Pat. No. 4,472,373 to Lyons; U.S. Pat. No. 4,083,955, to Grabenstetter et al., all of which are incorporated herein by reference.

Finally, as part of the pharmaceutical carrier of the compositions of the present invention which will be used in an aqueous media (e.g., oral compositions to be used in the oral cavity; body rinses to treat acne; vaginal douches), it is preferred that the compositions comprise a boron-containing aliphatic peroxy acid-stabilizing agent. The use of such stabilizing agents is disclosed in the concurrently filed, copending patent application of Sampathkumar having U.S. Ser. No. 811,148, filed Dec. 19, 1985, now abandoned. In addition, it is preferred that such compositions comprise a pharmaceutically-acceptable carrier capable of buffering the composition during use to a pH within the range of about 5 to about 10, more preferably from about 7.0 to about 9.0, and most preferably from about 8.0 to about 9.0. Non-limiting examples of buffers for use in the pharmaceutically-acceptable carrier include citrate, citrate/bicarbonate, phosphate, and especially borate buffers.

Method of Treating Anaerobic Bacterial Infections

The present invention also relates to a method for treating or preventing anaerobic bacterial infections, especially diseases of the oral cavity, in humans or lower animals. Such a method comprises administering to said human or lower animals a safe and effective amount of the peroxy acid of substituted or unsubstituted 1,12-dodecanedioic acid, or its pharmaceutically-acceptable salts or esters. Anaerobic bacterial infections which are particularly suited for treatment by the method of the present invention are those which may be treated by topical application of the antibacterial agent. Generally, tissues that may be treated by topical application are external mucous membrane and mucocutaneous orifices.

Non-limiting examples of anaerobe infections which may be treated by the method of the present invention include anaerobe infections of the skin or soft tissue (e.g., acne, dandruff, gas gangrene, gas-warming cellulitis, perirectal abscess, breast abscess, dermatological lesions, wound infections, bovine mastitis), the vagina, (e.g., vulvovaginal abscess), the uterus (e.g., uterine infection), urinary tract infections, the eyes (e.g., conjunctivitis, lid infection), the ears (e.g., otitis media, mastoiditis), the sinuses (e.g., sinusitis), and diseases of the oral cavity (e.g., Vincent's disease, periodontal disease). Generally not included under the method of treatment in the present invention are internal anaerobe infections that require enteral or systemic treatment methods to deliver the active to the infected tissue, such as abdominal infections, cardiovascular infections, central nervous system infections, lung infections, stomach and intestinal infections, and bone and joint infections. Specific anaerobe infections are more fully disclosed in Finegold's *Anaerobic Bacteria in Human Disease*, (Academic Press, Inc., New York, 1977), and in *Anaerobic Bacteria:Role in Disease* (published by Charles C. Thomas, Springfield, Ill.; Albert Balows, et al., editors; 1974).

The term "diseases of the oral cavity", as used herein, means diseases which are initiated and/or perpetuated by bacteria in the oral cavity, especially anaerobic bacteria, and includes such diseases as, for example, periodontal disease, gingivitis, periodontitis, gingivosis, periodontosis, periodontitis complex, and other inflammatory and/or degenerative conditions of the tissue within the oral cavity, plus caries, Vincent's disease, trench mouth, and malodor. Also, specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, *Anaerobic Bacteria in Human Diseases*, Chapter 4, pages 78–104, and Chapter 6, pages 115–154 (Academic Press, Inc., New York, 1977). The method of treatment of the present invention is particularly effective for treating or preventing periodontal disease, gingivitis and/or periodontitis.

The term "safe and effective amount", as used herein, means an amount of a peroxy acid of substituted or unsubstituted 1,12-dodecanedioic acid, or its pharmaceutically-acceptable salts or esters, which is sufficient to significantly reduce the severity of the infection being treated, but low enough to avoid serious side effects (at a reasonable benefit/risk ratio), within the scope of sound medical judgement. The safe and effective amount of an antibacterial agent of the present invention will vary with the particular infection (e.g., disease of the oral cavity) being treated, the age and physical condition of the patient being treated, the severity of the infection, the duration of treatment, the nature of concurrent therapy, the specific form (i.e., acid, salt and/or ester) of the antibacterial agent employed, the particular vehicle from which the antibacterial agent is applied, and like factors within the knowledge and expertise of the attending physician.

Generally, a safe and effective amount is greater than about $1 \times 10^{-4}$ grams of diperoxy 1,12-dodecanedioic acid per application, preferably within the range of from about $1 \times 10^{-4}$ grams to about 1 gram of diperoxy 1,12-dodecandedioic acid per application, more preferably from about $1 \times 10^{-4}$ grams to about 0.01 grams of diperoxy 1,12-dodecandioic acid per application. In addition, the concentration of the anaerobe-selective antibacterial agent in aqueous solutions topically applied to the infected area will be in the range by weight of from about 0.001% to about 10% (about 1.2 ppm to about 12,000 ppm available oxygen for diperoxy 1,12-dodecanedioic acid), preferably from about 0.001% to about 1% (about 1.2 ppm to about 1,200 ppm available oxygen for diperoxy 1,12-dodecanedioic acid), more preferred being from about 0.01% to about 1% (about 12 ppm to about 1,200 ppm available oxygen for diperoxy 1,12-dodecanedioic acid), with from about 0.05% to about 0.5% (about 60 ppm to about 600 ppm available oxygen for diperoxy 1,12-dodecanedioic acid) being most preferred (especially for oral applications and to provide additional anti-caries benefits).

As noted, in order to effectively use the compositions of the present invention in the method of treatment of the present invention, it is generally necessary to apply such compositions within a relatively short period of time after exposing the peroxy acid-containing composition to water. For the rinse solutions of the present invention, it is preferred that they be utilized within about 30 seconds to about 1 minute after preparation of the aqueous solution to be applied. Time before application is generally less critical for other types of compositions of the present invention, for example those compositions which ordinarily would be exposed to significant amounts of water only at the beginning of their use (e.g., toothpaste, chewing gums, lozenges) or which are not exposed to water at all (e.g., creams or lotions for treating acne). The period of time between hydration and use is also less important when a component of the pharmaceutically-acceptable carrier comprises a material which stabilizes the peroxy acid antibacterial agent against deactivation.

The following examples illustrate the anaerobe-selective antibacterial compositions and methods of the present invention, and the benefits achieved by the utilization of such compositions and methods. These examples are illustrative of the invention herein and are not to be construed as limiting thereof.

EXAMPLE 1

Mouth rinses according to the present invention have the following compositions:

| Component | Weight % | |
|---|---|---|
| | Composition A | Composition B |
| DPDA[1] | 0.1 | 0.2 |
| Boric acid | 0.133 | 0.266 |
| Sodium saccharin | 0.102 | 0.102 |
| Sodium borate[2] | 0.680 | 0.68 |
| 1N HCl | 1.2 | 1.2 |
| Ethanol | 15 | 15 |
| Water | Balance | Balance |

[1]diperoxy 1,12-dodecanedioic acid
[2]$Na_2B_4O_7 \cdot 10H_2O$

Composition A is prepared as follows: Add 1.0 g of 100% ethanol to a container along with 43.75 mg of a DPDA/boric acid mixture (a hydrate which contains approximately 20% water), and then vortex rapidly for 10 seconds. To this mixture add 14.0 g of a solution containing 9% ethanol, 0.73% sodium borate, 1.3% 1N HCl, 0.11% sodium saccharin, and 89% water (pH of solution approximately 8.5). Vortex the resulting mixture for another 10 seconds. As prepared, Composition A has an available oxygen concentration of approximately 120 ppm. Composition B is similarly prepared using the above procedure but substituting 87.5 mg of DPDA/boric acid for the 43.75 mg of DPDA/boric acid. As prepared, Composition B has an available oxygen concentration of approximately 240 ppm.

Compositions A and B are used twice daily within 10 minutes of mixing as a mouth rinse to treat or prevent gingivitis or periodontal disease, and to prevent caries.

EXAMPLE 2

Body rinses of the present invention for treating or preventing acne have the following compositions:

| Component | Weight % | |
|---|---|---|
| | Composition A | Composition B |
| DPDA[1] | 0.1 | 0.2 |
| Phosphate buffer (pH = 7) | 1 | 1 |
| Ethanol | 15 | 15 |
| Water | Balance | Balance |

[1]diperoxy 1,12-dodecanedioic acid

Compositions A and B are prepared as the compositions in Example 1. Compositions A and B are used immediately after preparation as body rinses to treat or prevent acne.

EXAMPLE 3

Several toothpaste or gel formulations according to the present invention are prepared using procedures taught in U.S. Pat. No. 3,988,433, issued Oct. 26, 1976 to Benedict. Compositions of such formulations are set forth as follows:

| | Weight % |
|---|---|
| Composition A | |
| DPDA[1] | 5% |
| Boric acid/borate (buffered to pH = 8.5) | 5% |
| Triacetin | Balance |
| Composition B | |
| DPDA[1] | 2% |
| Boric acid/borate (buffered to pH = 8.5) | 5% |
| Mineral oil (SSF-60) | Balance |
| Composition C | |
| DPDA[1] | 10% |
| Phosphate buffer (pH = 7.0) | 5% |
| Menthyl acetate and menthene (1:1) | 2% |
| Sodium alkyl ($C_{10}$–$C_{12}$) sulfate | 4% |
| Diethylether of polyethylene glycol (M.W. 1000) | Balance |
| Composition D[2] | |
| Component I: | |
| DPDA[1] | |

| -continued | Weight % |
|---|---|
| Potassium polyethyoxylated (4) coconut fatty alcohol sulfate | 4% |
| Methyl laurate | Balance |
| Component II: | |
| Dicalcium orthophosphate | 40% |
| Eucalyptol | 2% |
| Boric acid/borate (buffered to pH = 8.5) | 3% |
| NaF | 0.5% |
| Color | 0.1% |
| Methyl Laurate | Balance |

[1] diperoxy 1,12-dodecanedioic acid
[2] toothpaste composition D is formed upon mixing, by coextrusion from separate chambers of a toothpaste tube, components I and II in a 1:1 ratio just prior to use Brushing once a day for 30 seconds with 1 ml (approximately 1 gram) of any of the above described toothpastes or gels promotes continued gingival health in persons with healthy gingival tissue by significantly reducing the number of pathogenic bacteria in dental plaque. The compositions are also effective for treating gingivitis.

What is claimed is:

1. An anaerobe-selective antibacterial oral care composition useful for preventing or treating gingivitis or periodontal disease in the oral cavity comprising:
   (a) from about 0.01% to about 35% by weight of an anaerobeselective antibacterial agent selected from substituted and unsubstituted diperoxy 1,12-dodecanedioic acids, and their pharmaceutically-acceptable salts and esters; and
   (b) from about 65% to about 99.99% by weight of a pharmaceutically-acceptable carrier comprising a flavoring agent or a sweetening agent;
   said composition being in the form of a dentifrice (toothpaste tooth powder, tooth gel,), mouth rinse, mouth spray, lozenge, chewing gum or sachet.

2. An anaerobe-selective antibacterial composition according to claim 1 wherein the antibacterial agent is selected from unsubstituted diperoxy 1,12-dodecanedioic acid, its pharmaceutically-acceptable salts or esters, and mixtures of these agents.

3. An anaerobe-selective antibacterial composition according to claim 1 comprising:
   (a) from about 0.1% to about 10% by weight of unsubstituted diperoxy 1,12-dodecanedioic acid; and
   (b) from about 90% to about 99.9% by weight of the pharmaceutically-acceptable carrier.

4. An anaerobe-selective antibacterial composition according to claim 2 in the form of a lozenge or chewing gum.

5. An anaerobe-selective antibacterial composition according to claim 2 in the form of a mouth rinse wherein:
   (a) the antibacterial agent comprises from about 0.01% to about 10% by weight of the composition; and
   (b) the pharmaceutically-acceptable carrier comprises from about 90% to about 99.99% by weight of the composition, and further comprises one or more mouth rinse components selected from ethyl alcohol, water, humectants, sudsing agents, and mixtures of these components.

6. An anaerobe-selective antibacterial dentifrice composition comprising:
   (a) from about 1% to about 10% by weight of an antibacterial agent selected from diperoxy 1,12-dodecanedioic acid, its pharmaceutically-acceptable salts or esters, and mixtures of these agents; and
   (b) from about 90% to about 99% by weight of a pharmaceutically-acceptable carrier which comprises a dental abrasive polishing material and a flavoring agent or a sweetening agent.

7. An anaerobe-selective antibacterial dentifrice composition according to claim 6 wherein the pharmaceutically-acceptable carrier further comprises a water-soluble fluoride.

8. An anaerobe-selective antibacterial dentifrice composition according to claim 7 wherein the composition comprises a water-soluble fluoride compound selected from sodium fluoride, stannous fluoride, indium fluoride, sodium monofluorophosphate, and mixtures thereof.

* * * * *